United States Patent [19]

Borrega et al.

[11] Patent Number: 5,545,738

[45] Date of Patent: Aug. 13, 1996

[54] ALFUZOSIN HYDROCHLORIDE DIHYDRATE

[75] Inventors: Regis Borrega, Le Plessis Robinson, France; Satoshi Kitamura, Osaka, Japan

[73] Assignee: Synthelabo, Le Plessis-Robinson, France

[21] Appl. No.: 364,180

[22] Filed: Dec. 27, 1994

[30] Foreign Application Priority Data

Dec. 28, 1993 [JP] Japan ..................... 5-353828

[51] Int. Cl.$^6$ ............ A61K 31/505; C07D 405/12
[52] U.S. Cl. .................................... 544/291
[58] Field of Search ............... 544/291; 514/259

[56] References Cited

U.S. PATENT DOCUMENTS

| | | | |
|---|---|---|---|
| 4,251,532 | 2/1981 | Roteman | 544/291 |
| 4,661,491 | 4/1987 | Regnier | 514/260 |
| 4,873,330 | 10/1989 | Lindholm | 544/291 |
| 4,925,837 | 5/1990 | Cavero et al. | 514/211 |
| 5,294,615 | 3/1994 | Meyer et al. | 514/254 |

*Primary Examiner*—Mukund J. Shah
*Assistant Examiner*—Matthew V. Grumbling
*Attorney, Agent, or Firm*—Jacobson, Price, Holman & Stern, PLLC

[57] ABSTRACT

Alfuzosin hydrochloride is stabilized as alfuzosin hydrochloride dihydrate, which is useful for the production of antihypertensive agents or dysuria curing agents.

3 Claims, 7 Drawing Sheets

ALFUZOSIN HYDROCHLORIDE DIHYDRATE

The present invention belongs to the field of synthetic medicinal chemistry, and it relates to the stabilization of the publicly known compound, alfuzosin hydrochloride. Particularly, the present invention relates to a hydrate of alfuzosin hydrochloride.

Alfuzosin hydrochloride is a compound represented by the formula:

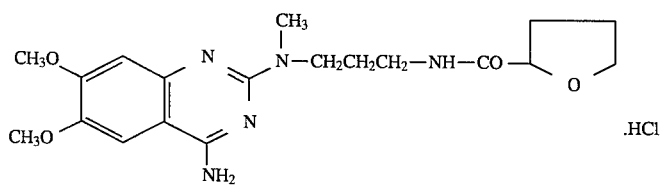

.HCl and is described in Japanese Examined Patent Application Publication SHO No. 60-23114. This compound is known to be an antagonist of $\alpha_1$-adrenergic receptor, and is useful as antihypertensive agent and dysuria curing agent (see also Japanese Examined Patent Application Publication HEI No. 5-64930).

Generally, it is known that active components or excipients undergo crystal transition due to moisture absorption, which results in their volumetric change, leading to a change in hardness or cracking of the tablets. To establish appropriate bioavailability, such changes are extremely troublesome phenomena, particularly in the case of sustained release preparations. When anhydrous alfuzosin hydrochloride is preserved under conditions with the relative humidity exceeding 75%, the crystal structure of the anhydrous form changes, thereby providing a trihydrate, which is accompanied by a change in volume. No reports have been made concerning the change in the preparation properties of tablets comprising crystals of anhydrous alfuzosin which are observed in long period stability tests, etc. To avoid the realization of the above-mentioned anxiety, however, it is useful to have an alfuzosin compound in a crystal state which does not suffer from the change in the crystal form under influence of humidity and temperature during the preparation process and storage of the preparations.

After repeated zealous investigations, we the present inventors have found that alfuzosin hydrochloride can take forms of mono-, di-, tri- and tetrahydrate, with confirmation that the dihydrate is the stablest of them during the usual preparation process and under usual preservation conditions, thus the present invention has been completed. Alfuzosin hydrochloride dihydrate is produced by recrystallization of anhydrous alfuzosin hydrochloride from an 80:20 mixture solution of acetone and water at 6° C.

The tetrahydrate of alfuzosin hydrochloride is produced by recrystallization under room temperature conditions in the same manner as its dihydrate.

The trihydrate of alfuzosin hydrochloride is produced by keeping anhydrous alfuzosin hydrochloride at 25° C. and at a relative humidity of 93% for three days. Here the monohydrate is believed to be obtained by allowing the trihydrate to stand under the conditions of 25° C. and at a relative humidity of 0% for two or more days.

EXAMPLES

Hereunder the present invention will be explained in detail with reference to the Examples, without limiting the scope of the present invention thereto.

Anhydrous alfuzosin hydrochloride and various hydrates thereof may be distinguished from each other by means of X-ray powder diffraction, IR spectra or thermal analysis. In the present examples, the distinguishing was conducted using X-ray powder diffraction capable of characterizing crystal structures, with investigation of moisture content carried out appropriately.

Here, the X-ray powder diffraction was carried out using Phillips MPD1880 X-ray diffraction apparatus system which uses CuK$\alpha$ radiation. This apparatus was set up as follows: tube voltage 40 kV, tube current 50 mA, scanning rate 0.02°/s, sampling time 0.2 seconds, measurement range $2\theta=2.5-32.5°$.

Patterns of X-ray powder diffraction for the anhydrous form, dihydrate, trihydrate and tetrahydrate of alfuzosin hydrochloride are shown in FIG. 1, FIG. 2, FIG. 3 and FIG. 4, respectively. The respective characteristic diffractometric peaks are as follows:

Anhydrous form: $2\theta=7.56°$

Dihydrate: $2\theta=6.36°, 8.07°, 9.78°$

Trihydrate: $2\theta=6.12°, 8.96°$

Tetrahydrate: $2\theta=6.04°, 8.37°$

The moisture content was measured with Karl Fischer Aquameter (Kyoto Electron Industry, MK-AII) for about 100 mg of a sample dissolved in methanol for moisture measurement. In turn, the dehydration behavior of the crystal water was measured by thermogravimetry and differential thermal analysis using TG/DTA200 thermogravimetric apparatus and SSC5030 Disc Station (Seiko). Concretely, approximately 5 mg of a sample was weighed into an open aluminum pan and analyzed at a rate of temperature increase of 10° C./m or 1° C./m. This analysis was carried out in a nitrogen atmosphere (flow rate: 100 ml/m).

Example 1

Preparation of Alfuzosin Hydrochloride Dihydrate

To 2g of alfuzosin hydrochloride (anhydrous form) produced as described in Japanese Examined Patent Application Publication SHO No. 60-23114, was added 20 ml of an acetone/water (4:1) mixture solution, and the mixture was heated to reflux at approximately 60° C. until the anhydrous form was completely dissolved. After confirmation of the complete dissolution of the anhydrous form, the mixture was gradually cooled to room temperature, and the resulting precipitate was filtered off on filter paper, followed by air-drying at room temperature for 24 hours.

The obtained substance was confirmed to be alfuzosin hydrochloride dihydrate by X-ray powder diffraction.

Reference 1

Preparation of atfuzosin hydrochloride tetrahydrate

To 2 g of alfuzosin hydrochloride (anhydrous form) described in Japanese Examined Patent Application Publication SHO No. 60-23114, was added 20 ml of an acetone/water (4:1) mixture solution, after which themixture was shaken for mixing at room temperature.

The anhydrous formwas dissolved, but a precipitate was observed immediately upon stoppage of stirring. The resulting precipitate was filtered off on filter paper and air-dried at room temperature for 24 hours.

The obtained substance was confirmed to be alfuzosin hydrochloride tetrahydrate by X-ray powder diffraction.

The stability of alfuzosin hydrochloride dihydrate of the present invention was evaluated according to the following tests.

Test 1

Hygroscopicity Test

A 0.2 g-portion of a sample of each of the anhydrous form and respective hydrates of alfuzosin hydrochloride was placed in a desiccator containing a saturated solution of the salts listed hereunder (at 25° C.), and the relationship between the relative humidity at which the hydrated states of the respective compounds become. stable physically and the hygroscopicity of polymorphic hydrated forms of those compounds was investigated. The respective samples were brought to equilibrium by storage for 10 days under the respective conditions. For the setting up of the relative humidity (RH: %) was used a saturated solution of salts listed below:

RH 0%, dry $P_2O_5$; RH 11%, LiCl; RH 22%, $CH_3COOK$; RH 33%, $MgCl_2$; RH 43%, $K_2CO_3.2H_2O$; RH 53%, $Mg(NO_3)_2$; RH 64%, $CoCl_2.6H_2O$; RH 75%, NaCl; RH 84%, KCl; RH 93%, $KNO_3$; RH 100%, water.

The obtained results were graphed and shown in FIG. 5 attached hereto.

The anhydrous form of alfuzosin hydrochloride was stable at an RH of 75% or less. When preserved under conditions where the RH was over 75%, however, the moisture content increased significantly. This increasing continued until the moisture content attained the equilibrium of 12%, which is equivalent to 3 moles of water.

Under all the conditions relating to the relative humidity at 25° C., with exception under drying conditions (RH: 0%), all the hydrates did not undergo moisture absorption. With consideration for the fact that the relative humidity usually ranges from about 40% to about 80%, it may be concluded that all the hydrates including the dihydrate of the present invention do not cause moisture absorption at usual relative humidity at normal temperature.

Test 2

Drying Test

Different from the hygroscopicity test mentioned above, the various hydrates of alfuzosin hydrochloride were kept under drying conditions for the monitoring of the change in moisture content.

The obtained results are shown in FIG. 6 attached hereto. FIG. 6 shows that the dehydration process of alfuzosin hydrochloride dihydrate goes very slowly. That is, although the trihydrate and tetrahydrate lost most of the water in 1 day, no significant change in moisture content was observed for the dihydrate according to the present invention even in 3 days. This evidences that the interaction between alfuzosin hydrochloride and water molecules is stronger in the case where the former is a dihydrate than in the case of a trihydrate or tetrahydrate.

In this connection, simultaneously in the present test, also the crystal state of dried samples after a three-days' drying was investigated for the dihydrate of the present invention by X-ray powder diffraction under drying conditions, for comparison with patterns of X-ray powder diffraction under normal conditions. As a result, it has been revealed that the dihydrate of the present invention retains its original crystal form, with some drop in degree of crystallization (data not shown).

Test 3

Test on Stability to Heating, Humidifying and Light

The stability test was carried out following the procedures described below.

A 0.3 g-portion of each of the anhydrous form and respective hydrates of alfuzosin hydrochloride in crystal forms was placed in a glass bottle (sealed) and in a desiccator filled with a NaCl saturated solution, and preserved at 70° C. with a heater (Toyama Industry), after which the physicochemical stability of each compound was evaluated by X-ray powder diffraction and high performance liquid chromatography (HPLC).

Separately, 0.3 g of each of the anhydrous form and respective hydrates of alfuzosin hydrochloride in crystal forms was placed in a plastic dish which was then covered with a polyvinylidene chloride film, followed by irradiation with a chemical lamp (dominant wavelength: 365 nm) for 24 hours, for the evaluation of the light stability in the same manner as in the above.

The obtained results are shown in the following table 1. Table 1 includes the moisture content of the respective crystal forms as well. Here, the HPLC was carried out under the following conditions:

HPLC apparatus (manufactured by Shimazu)

Detection with UV (at 254 nm); column (Nucleosil $5C_{18}$, 150 mm×4 mm, M, Nagel; flow rate 1.0 ml/m; room temperature; eluent, $NaClO_4$ (in 1000 ml of water, 7 g, pH 3.5)- acetonitrile-THF (155:55:45): internal standard, p-chloroacetanilide (0.5 mg/ml).

[TABLE 1]

| Crystal forms (moisture content: %) | Results of the stability test | | | |
|---|---|---|---|---|
| | 70° C. 9 days (moisture content: %) | 70° C. 9 days at RH 75% (moisture content: %) | | Chemical lamp (moisture content: %) |
| Anhydrous (0.1%) | Stable (1.33%) | Stable (0.7%) | | Stable (0.66%) |
| Dihydrate (DI) (8.14%) | Stable (8.41%) | Stable (8.48%) | | Stable (8.40%) |
| Trihydrate (TRI) (12.75%) | DI = 37% + TRI = 68% (11.05%) | DI = 16% + TRI = 84% (12.03%) | | Stable (12.87%) |
| Tetrahydrate (TETRA) (14.93%) | DI = 26% + TETRA = 74% (13.19%) | DI = 98% + TETRA = 2% (8.25%) | | Stable (15.18%) |

The above table 1 proves that the anhydrous form and dihydrate are extremely stable under all these conditions. On the other hand, both the trihydrate and tetrahydrate changed partially into the dihydrate, so they are considered unstable under the two conditions mentioned above.

To light, neither chemical decomposition nor physical change was found for all the samples.

Test 4

Accelerated Test

A 0.3 g-portion of each of the hydrates of alfuzosin hydrochloride was preserved in heaters (Sanyo) set to 100° C. and 120° C., for the confirmation of the stability of the respective hydrates. The physical stability of the respective samples was confirmed by X-ray powder diffraction.

The obtained results are shown in the following tables 2 and 3.

[TABLE 2]

| | Accelerated test at 100° C. | | | |
|---|---|---|---|---|
| | Preservation time | | | |
| Crystal forms | 30 min. | 60 min. | 90 min. | 120 min. |
| Dihydrate (DI) | DI | DI | DI | DI |
| Trihydrate (TRI) | TRI | TRI + DI | TRI + DI | TRI + DI |
| Tetrahydrate (TETRA) | TETRA + DI | DI | DI | DI |

In this test, the crystal state of the respective hydrates was monitored by X-ray powder diffraction every 30 minutes for 2 hours.

The dihydrate was stable for 2 hours.

The trihydrate changed into the dihydrate by degrees.

Also the tetrahydrate changed into the dihydrate by degrees.

[TABLE 3]

| | Accelerated test at 120° C. |
|---|---|
| Crystal forms | Preservation time 45 min. |
| Dihydrate (DI) | DI |
| Trihydrate (TRI) | AN + DI + TRI |
| Tetrahydrate (TETRA) | DI |

[wherein AN stands for anhydrous form.]

The dihydrate was stable for 45 minutes.

The trihydrate changed into a mixture of the anhydrous form, dihydrate and trihydrate.

The tetrahydrate changed into the dihydrate.

With the results of the above-mentioned tests 1–4, it may be concluded that the stablest crystal form of alfuzosin hydrochloride under normal preservation conditions for the preparations (e.g., 25° C., relative humidity 40–80%) and under heating (drying) condition (e.g., 50°–60° C.) to be expected for the preparation process is that of the dihydrate.

Test 5

Dissolution Test

Water at 37° C. was used to study the dissolution profiles of the respective hydrates of alfuzosin hydrochloride. The results are shown in FIG. 7. FIG. 7 proves that the respective hydrates have dissolution profiles which are very similar to those of anhydrous alfuzosin hydrochloride. This is indicative of the fact that all the hydrates, including the dihydrate of the present invention, may be used for the preparation of alfuzosin hydrochloride preparations in the same manner as its anhydrous form.

Accordingly, the dihydrate according to the present invention may be used for the production of antihypertensive agents or dysuria curing agents.

Claimed is:

1. Alfuzosin hydrochloride dihydrate.

Figure 1:
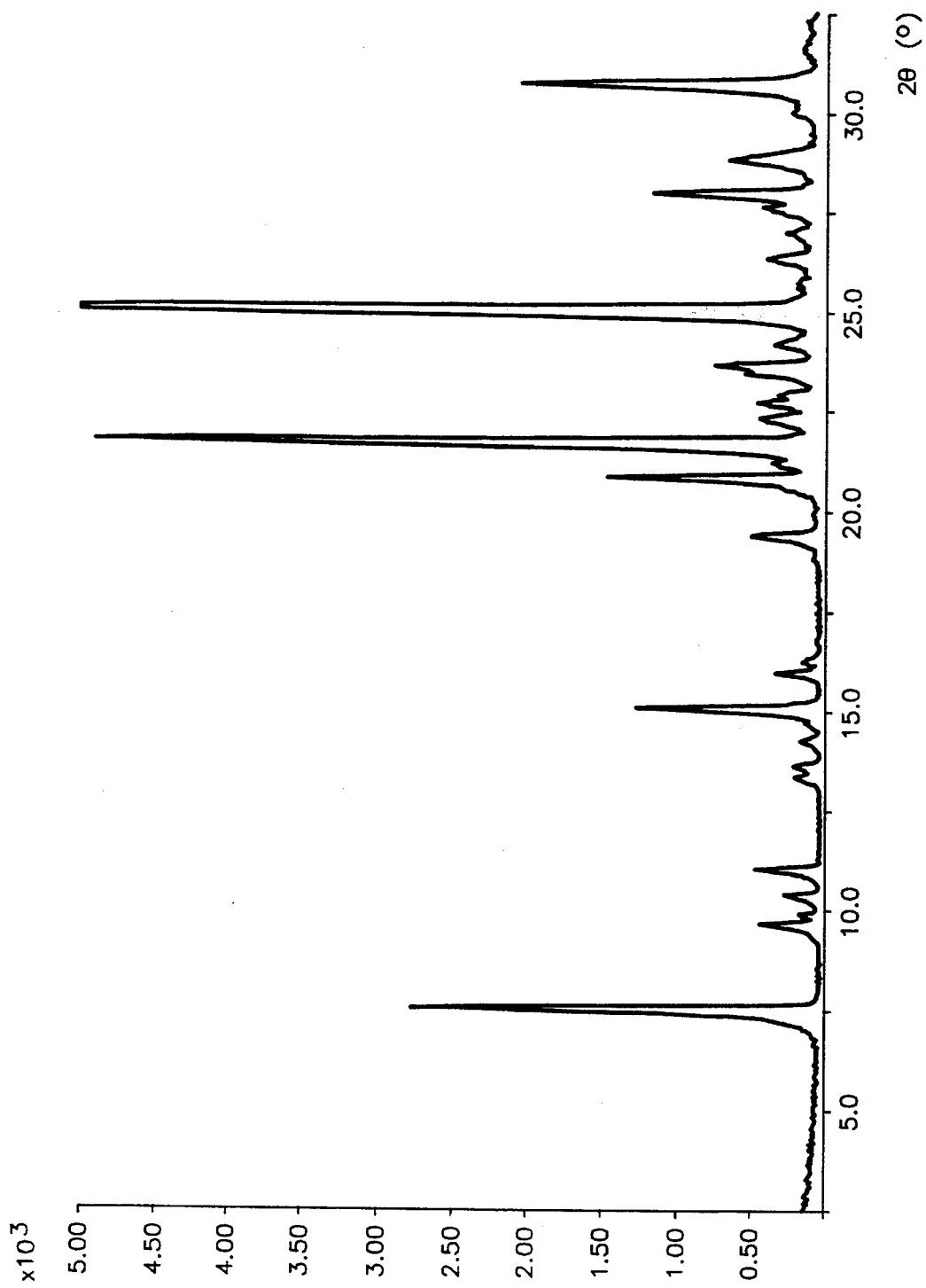
FIG. 1 is a chart showing the X-ray powder diffraction pattern of anhydrous alfuzosin hydrochloride.
Figure 2:
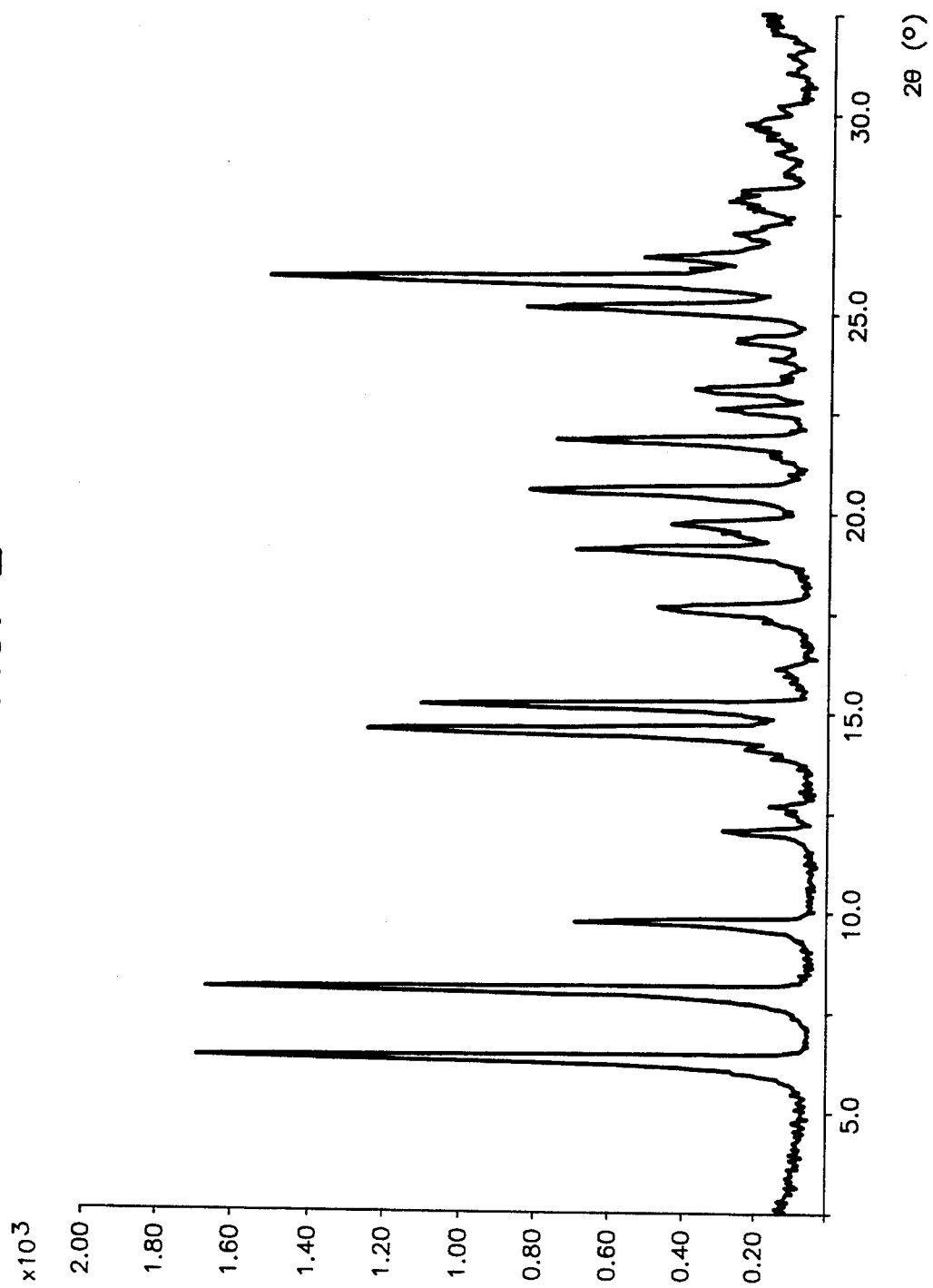
FIG. 2 is a chart showing the X-ray powder diffraction pattern of alfuzosin hydrochloride dihydrate.
Figure 3:
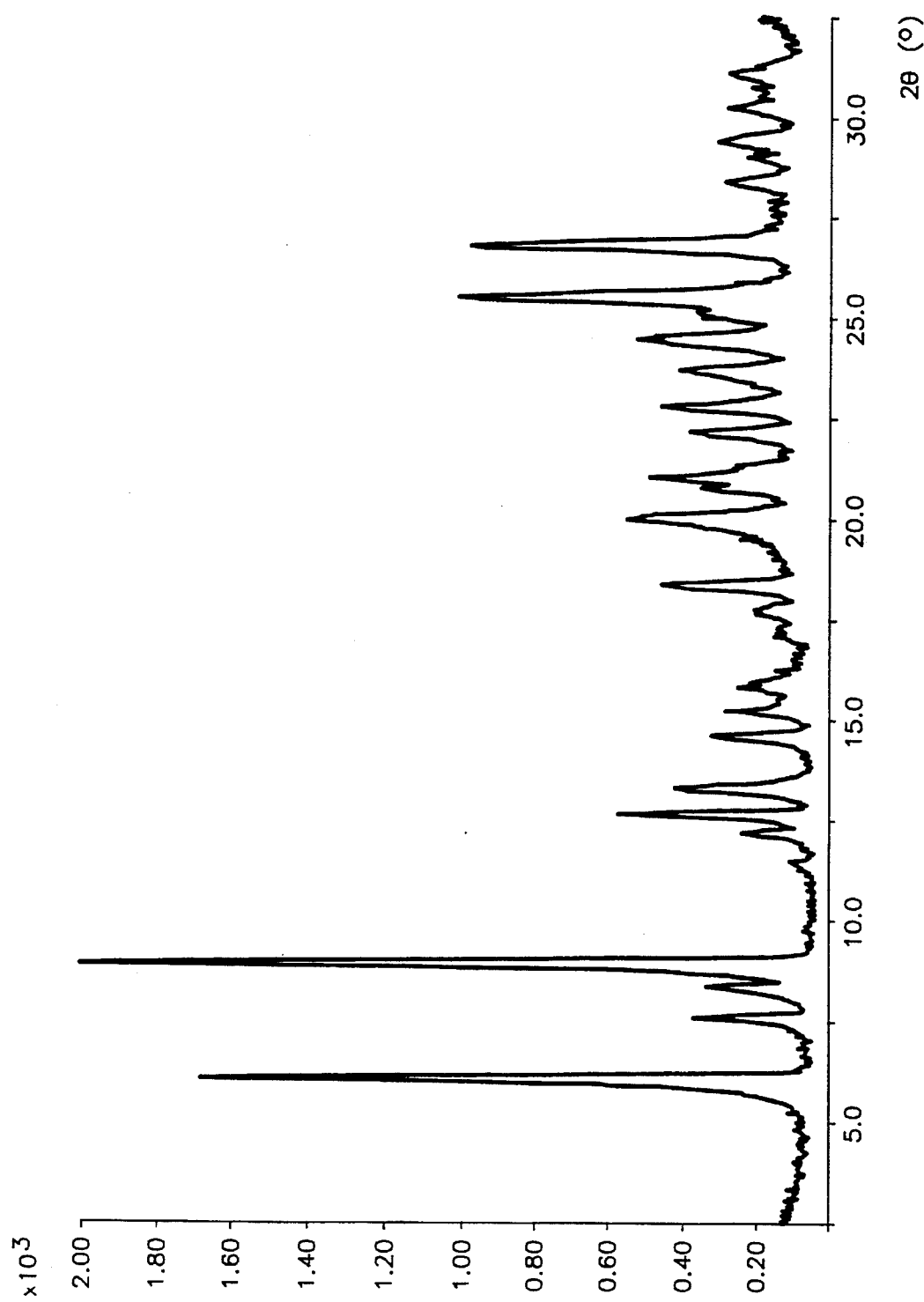
FIG. 3 is a chart showing the X-ray powder diffraction pattern of alfuzosin hydrochloride trihydrate.
Figure 4:
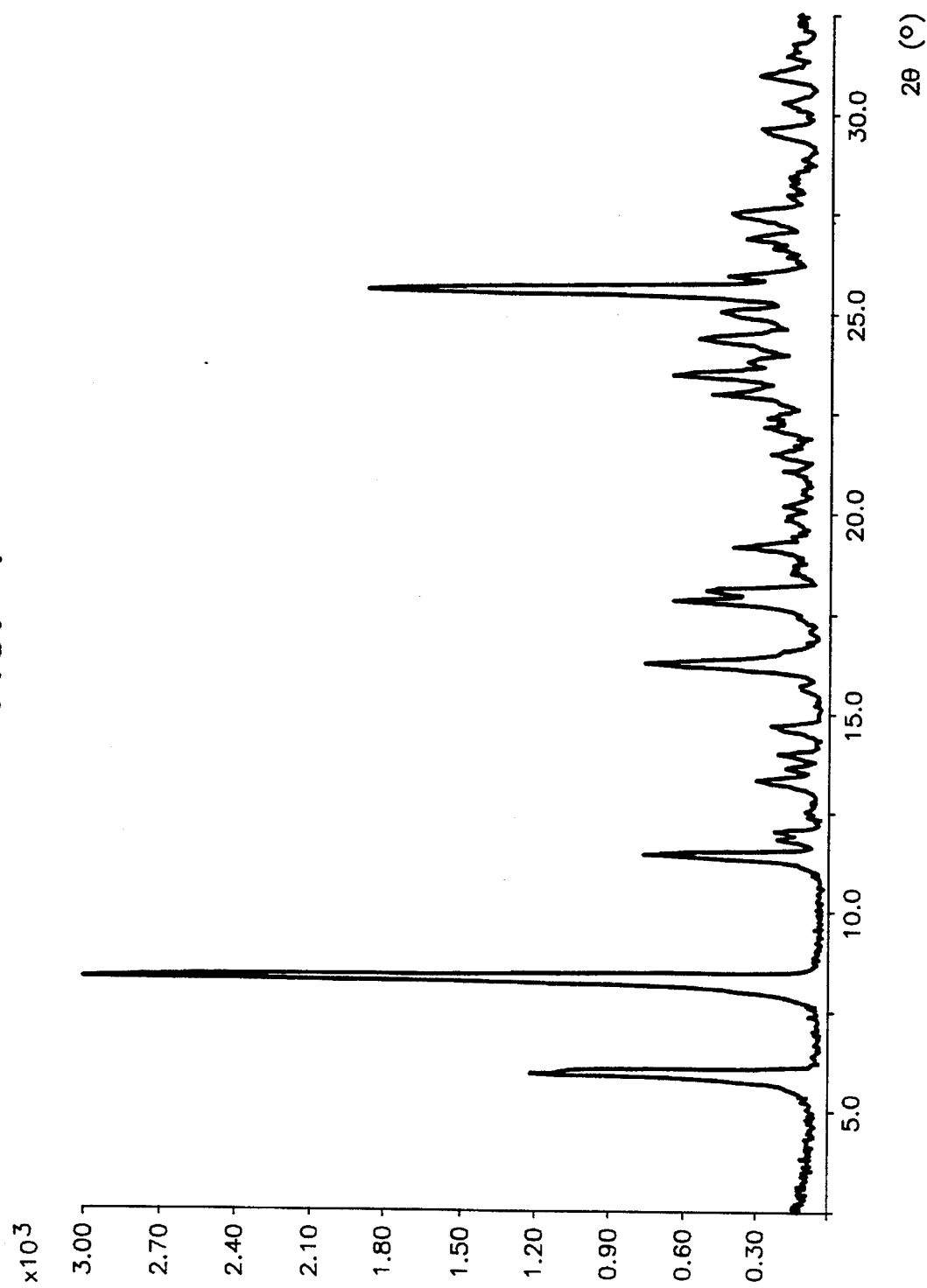
FIG. 4 is a chart showing the X-ray powder diffraction pattern of alfuzosin hydrochloride tetrahydrate.
Figure 5:
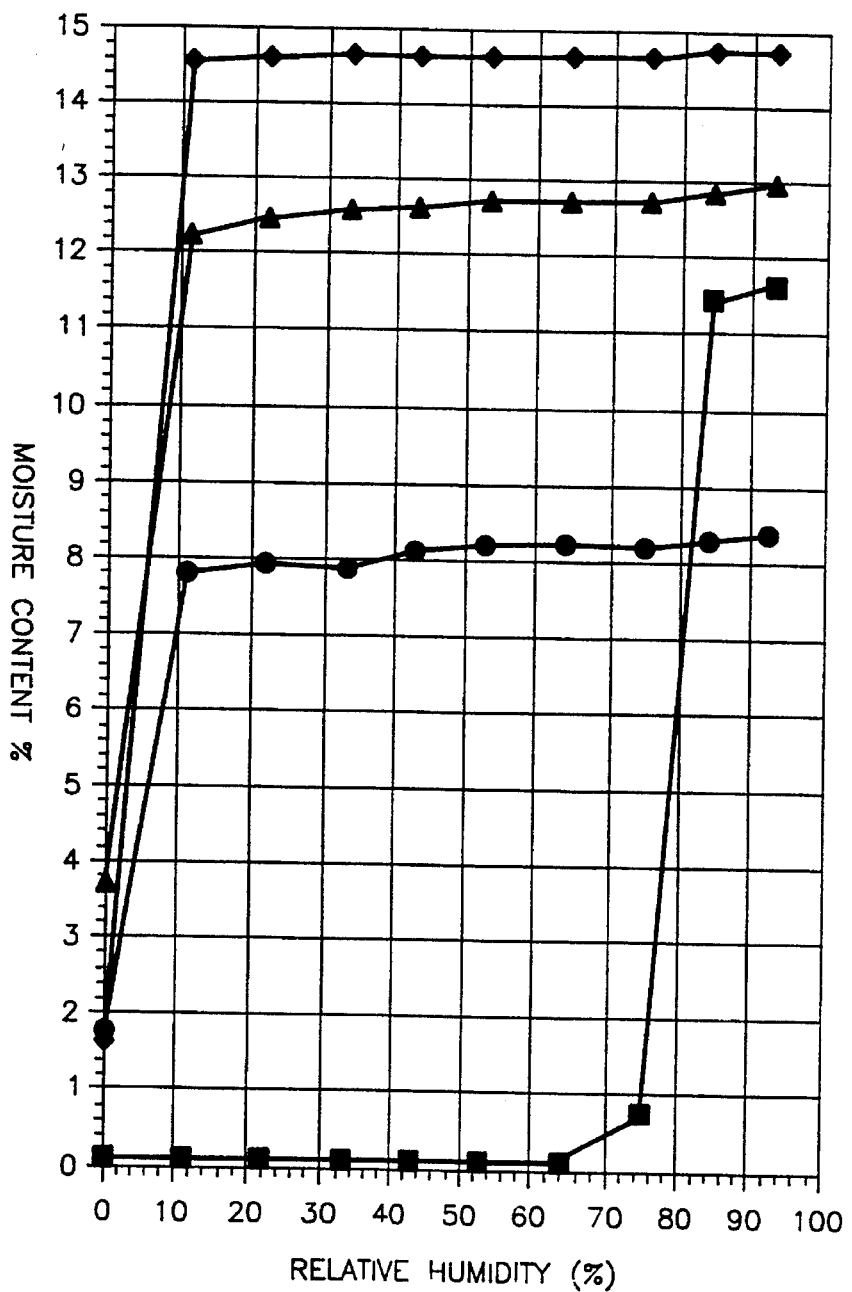
FIG. 5 is a graph showing the hygroscopicity of the anhydrous form of alfuzosin hydrochloride and its various hydrates.
Figure 6:
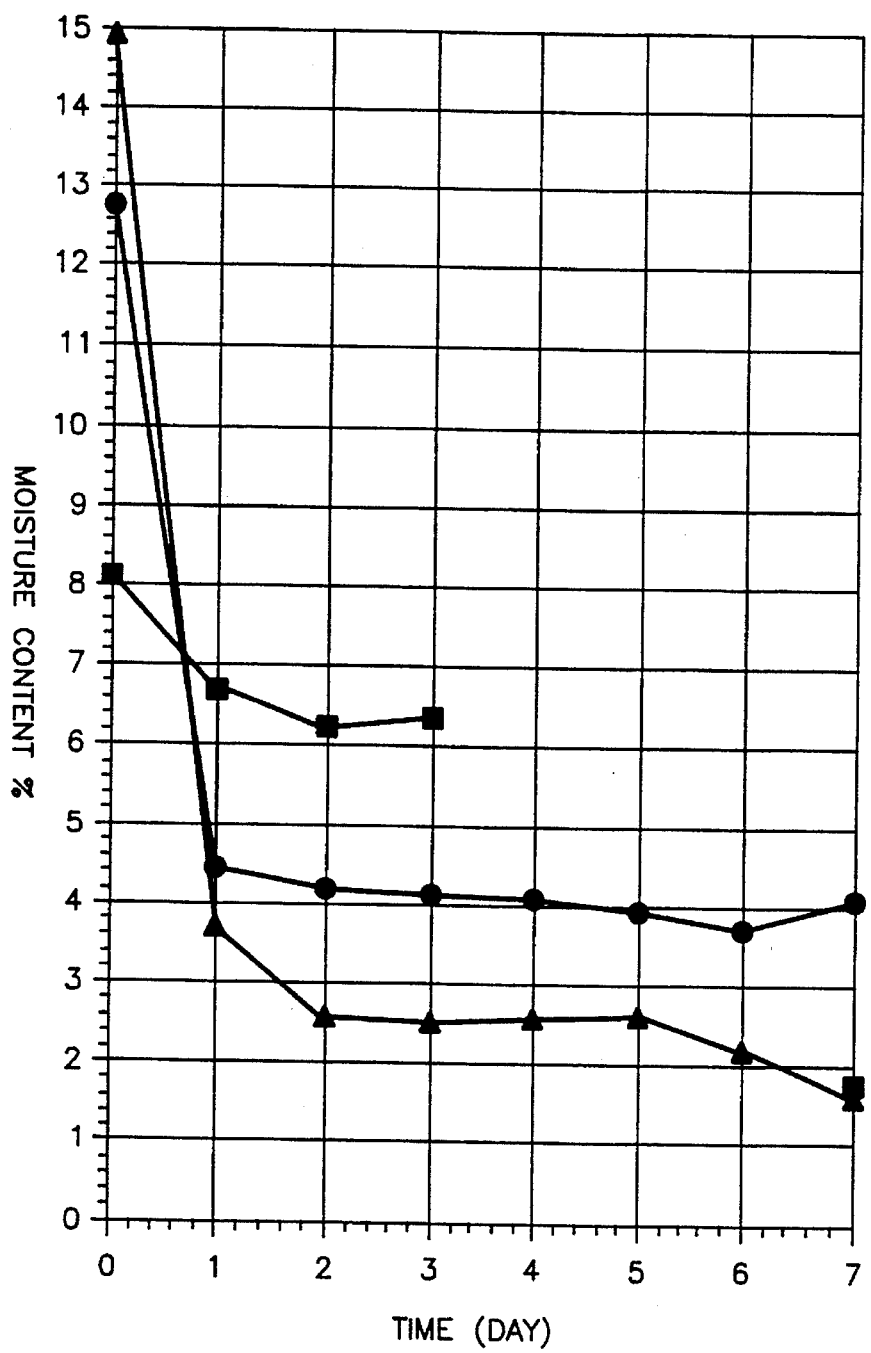
FIG. 6 is a graph showing the change in the moisture contents of the hydrates of alfuzosin hydrochloride under drying conditions.
Figure 7:
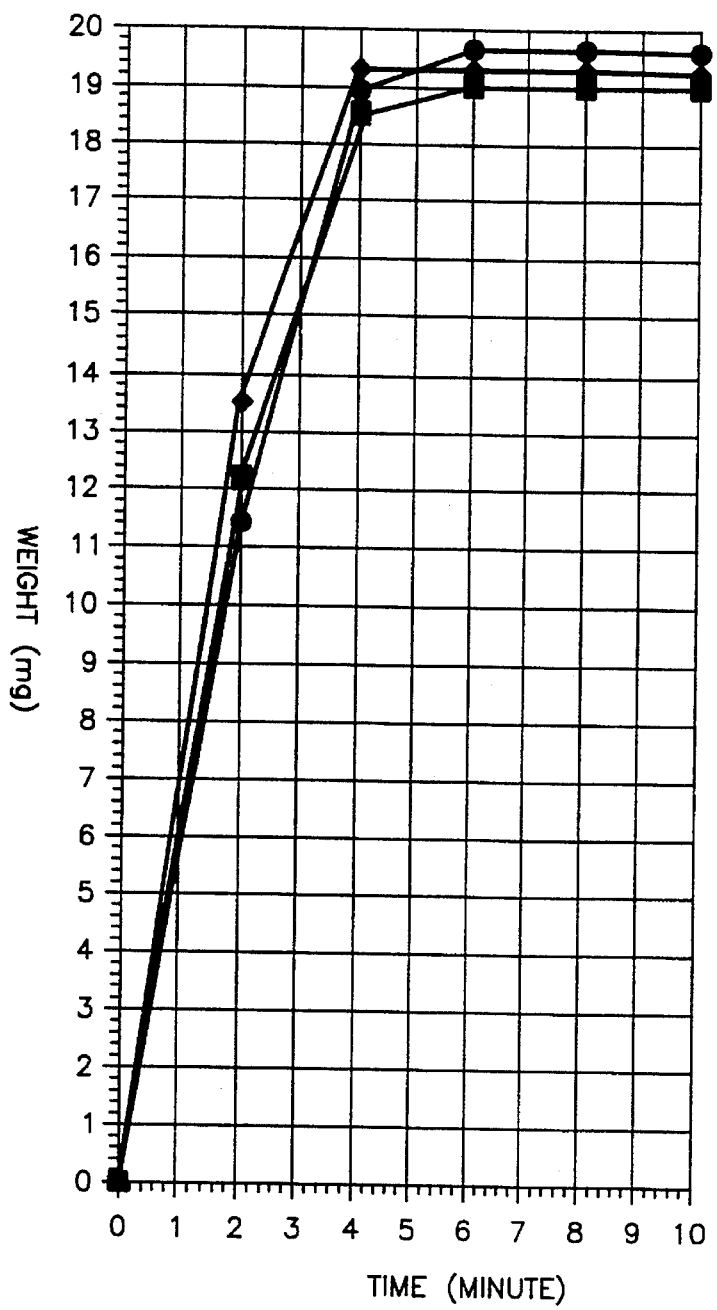
FIG. 7 is a graph showing the dissolution profiles of the anhydrous form and respective hydrates of alfuzosin hydrochloride in water at 37° C.

2. A hydrate of alfuzosin hydrochloride having the X-ray powder diffraction pattern shown in FIG. 2.

3. A hydrate of alfuzosin hydrochloride having an X-ray powder diffraction pattern with characteristic diffractomeric peaks $2\theta = 6.36°, 8.07°, 9.78°$.

* * * * *